(12) United States Patent
Andrews

(10) Patent No.: US 8,282,394 B2
(45) Date of Patent: Oct. 9, 2012

(54) DENTAL ARTICULATOR APPARATUS HAVING VISIBLE CODING OF TEETH AND JAW POSITIONS WITH RESPECT TO POST-TREATMENT GOALS

(76) Inventor: Lawrence F. Andrews, La Jolla, CA (US)

( * ) Notice: Subject to any disclaimer, the term of this patent is extended or adjusted under 35 U.S.C. 154(b) by 147 days.

(21) Appl. No.: 12/653,132

(22) Filed: Dec. 8, 2009

(65) Prior Publication Data
US 2010/0092909 A1   Apr. 15, 2010

Related U.S. Application Data

(63) Continuation of application No. 11/546,817, filed on Oct. 11, 2006.

(51) Int. Cl.
*A61C 3/00* (2006.01)
(52) U.S. Cl. ........................................ 433/54
(58) Field of Classification Search ............ 433/60, 433/66, 73, 54
See application file for complete search history.

(56) References Cited

U.S. PATENT DOCUMENTS

| 2,430,525 | A * | 11/1947 | Miller | 433/54 |
| 4,171,570 | A | 10/1979 | Seldin | 433/73 |
| 4,189,835 | A | 2/1980 | Seldin | 433/214 |
| 5,176,515 | A | 1/1993 | Andrews | 433/24 |
| 5,498,158 | A | 3/1996 | Wong | 433/102 |
| D399,318 | S | 10/1998 | Andrews | D24/181 |
| D399,319 | S | 10/1998 | Andrews | D24/181 |
| 5,842,857 | A | 12/1998 | Andrews | 433/60 |
| 6,015,291 | A | 1/2000 | Cramer et al. | 433/57 |
| 6,109,917 | A | 8/2000 | Lee et al. | 433/73 |
| 6,198,807 | B1 | 3/2001 | DeSena | 378/165 |
| 6,520,676 | B1 | 2/2003 | Schmitz | 378/191 |
| 6,582,931 | B1 | 6/2003 | Kois et al. | 433/56 |
| 2004/0259050 | A1 | 12/2004 | Racich et al. | 433/56 |
| 2005/0089815 | A1 | 4/2005 | Lee | 433/60 |
| 2006/0204920 | A1 * | 9/2006 | Costello | 433/57 |

OTHER PUBLICATIONS

Andrews LF. The six keys to normal occlusion. Am. J. Orthod. 1972; 62:296-309.
Andrews LF. Straight wire, the concept and appliance. San Diego, LA Wells Co. 1989; 13-24.
Andrews LF. Syllabus of the Andrews orthodontic philosophy. 2001: 9$^{th}$ ed.
Andrews LF, ed. Andrews Journal of Orthodontics and Orofacial Harmony. 2000; 1: 1-60.
Clark JR, et al. Functional Occlusion: II. The role of articulators in orthodontics. 2001: J. Orth. 2001;28-2: 173-177.
Schlosser JB, et al. The effects of computer-aided anteroposterior maxillary incisor movement on ratings of facial attractiveness. Am. J. Orthod. & Dentofacial Orthop. Jan. 2005;127(1):17-24.
Golden Eagle Orthodontics, Inc. Instruction Manual for the Andrews Occlusofacial Simulator System (OFSS). No Date: 1-25.

* cited by examiner

*Primary Examiner* — Ralph Lewis
(74) *Attorney, Agent, or Firm* — INCAPLAW; Terrance A. Meador

(57) ABSTRACT

A visible coding of components of an articulator apparatus that mount maxillary and mandible casts indicates the relative correspondence between post-treatment goals and the present locations of a person's teeth and jaws. From another aspect, the visible coding indicates at least a direction, and preferably, a direction and a distance, which a person's teeth and/or jaws must be moved to achieve the goals.

2 Claims, 3 Drawing Sheets

DENTAL ARTICULATOR APPARATUS HAVING VISIBLE CODING OF TEETH AND JAW POSITIONS WITH RESPECT TO POST-TREATMENT GOALS

PRIORITY

This application is a continuation of co-pending U.S. patent application Ser. No. 11/546,817 filed Oct. 11, 2006.

BACKGROUND

In the fields of orthodontics and maxillofacial surgery, a dental articulator apparatus includes visible coding on articulator components to indicate the present positions of a person's teeth and jaws with respect to goals of orthodontic and/or surgical treatment. From another aspect, the visible coding indicates at least a direction, and preferably, a direction and a distance, which a person's teeth and/or jaws must be moved by orthodontics treatment and/or by surgery to achieve the goals.

Orthodontic practice has undergone a significant evolution in the past fifty years, with new diagnostic and treatment techniques emerging and rapidly replacing the standard practices of the preceding century. In the 1950s and 1960s, research was undertaken to determine optimal occlusion, in terms of quantifying dental arch characteristics and tooth positions of naturally optimal dentitions. See Andrews, L F. The Six Keys To Normal Occlusion. Am. J. Orthod. 1972; 62:296-309. See also Andrews L F. Straight Wire, The Concept and Appliance. San Diego: LA Wells Co; 1989; 407 p. Since 1970, this information has been practiced by orthodontists worldwide. From 1970 to 1990, research was undertaken to learn if individuals with balanced faces shared arch and jaw position characteristics. Such characteristics were found and reported. See Andrews L F, Andrews W A. Syllabus of the Andrews Orthodontic Philosophy, 9$^{th}$ edition, 2001, and Andrews L F, ed. Six Elements Orthodontics. The Andrews Journal of Orthodontics and Orofacial Harmony. 2000; 1: 8-33. This information has led to a method of orthodontic analysis and treatment called the Six Elements of Orofacial Harmony™.

According, to the Six Elements method, analysis of the relationship between the teeth, the jaws, and the face of a person is conducted using a set of goals (the Six Elements). The quality of the positions of the teeth or jaws relative to an Element is measured relative to anatomical landmarks. In this regard, an anatomical landmark is an anatomical point or line having a uniquely correct aesthetic and positional relationship with the teeth or jaws when they are optimally positioned. For example, optimal arch shape (Element I), is measured relative to the Wala ridge. And, optimal tooth positions are measured relative to the occlusal plane. For optimal orofacial harmony, the teeth and jaws are measured with respect to anatomical landmarks that relate optimal occlusion to facial balance. By way of illustration, one such landmark, used to determine anteroposterior (AP) jaw position, is the Goal Anterior Limit Line (GALL). The GALL is defined with respect to a Facial Axis Point (FA Pt) on the forehead and is located on the face, at or anterior to, the FA Pt in respect to the inclination of the forehead. The optimal locations of the upper and lower jaws are defined relative to the GALL. AP jaw positions are considered to be optimal when both arches are optimal. (Element I), interarch relationship is optimal (Key I of the Six Keys), and the FA Pt of the maxillary central incisor touches the GALL. See Schlosser J B, Preston C B, Lampasso J. The effects of computer-aided anteroposterior maxillary incisor movement on ratings of facial attractiveness. Am. J. Orthod. & Dentofacial Orthop. 2005 January; 127(1):17-24. See also, The Andrews Journal of Orthodontics and Orofacial Harmony. 2000; 1: 8-33.

Orthodontic practice has historically utilized a number of useful tools to assess dental condition, to aid in diagnosis and treatment planning, and to counsel patients. For example, models of a person's teeth and jaws are taken in the form of maxillary (upper jaw) and mandibular (lower jaw) casts. The casts are mounted on a machine called an articulator, which represents the bony skeleton of the jaws and jaw joints. See U.S. Pat. No. 5,176,515. See also the Occlusofacial Simulator System available from Golden Eagle Orthodontics, Inc. and described at the website accessed through www(dot)geo-orthodontics(dot)com. Casts are located on the articulator in the same orientation to the jaw joints, planes of the head, and each other as the teeth and jaws are on the person. Thus, when mounted on an articulator, the casts provide an orthodontist and/or a maxillofacial surgeon with a model that simulates the person's oral condition. That information, along with photographs, x-rays, and charts, allows the person's orofacial condition to be measured and helps the practitioner to determine a course of treatment designed to position the person's teeth and/or jaws with respect to goals of the treatment. When treatment is completed, final records can be taken to record and assess the quality of the treatment.

Designs of orthodontic diagnostic tools have changed to accommodate the needs of the new diagnostic techniques. For example, some articulators have been adapted to illustrate a person's pretreatment condition with respect to certain landmarks that help define a desired post-treatment condition. Relatedly, the Occlusofacial Simulator Articulator System available from Golden Eagle Orthodontics employs a simulated temporomandibular joint (TMJ), the posterior border of the oral complex, and a GALL rod mounted to a maxillary cast support member to show the proposed anterior border. However, other than for the posterior border, traditional articulators do not indicate where the pretreatment positions of teeth, arches, and jaws are with respect to intended positions, or where those pretreatment positions should be moved, in order to achieve specific post-treatment goals. Instead, such information is provided on patient charts, where the present positions of a person's teeth and jaws with respect to post-treatment goals are recorded in long hand or by means of coded markings.

As an example, the principal mode of recording a person's condition for diagnosis and treatment according to the Six Elements of Orofacial Harmony Philosophy uses intended goals or optimal outcomes. The present positions of the person's teeth and jaws are measured relative to optimal goals, which are the Six Elements of Orofacial Harmony or as close to them as circumstances permit. These measurements are recorded in the dental chart. The system of recordation may use colors, or words or letters that indicate colors, to signify the direction, and numbers to indicate the distance. Green (G) indicates that a measured position of a tooth, arch, or jaw is optimal with respect to a particular goal, which implies that no movement of teeth, arch, or jaw is necessary. Red (R) indicates that the position is anterior, superior, or buccal, relative to optimal, which implies that compensatory posterior, inferior, or lingual movement is necessary to achieve the goal. Black (B) indicates that the position is posterior, inferior, or lingual relative to optimal, which implies that compensatory anterior, superior, or buccal movement is necessary to achieve the goal. In each instance, if the amount of movement is interesting, it is entered in millimeters. See Andrews L F, ed. Six Elements Orthodontics. The Andrews Journal of Orthodontics and Orofacial Harmony. 2000; 1: pp. 24-25.

Presently, a practitioner cannot begin to plan, or visualize a manifold treatment strategy including movement of teeth and/or jaws simply by viewing an articulator with casts mounted thereto. Instead, other sources of information must be consulted while the articulator-mounted casts are studied. Separately, the diagnostic effort, and the attendant patient counseling, is encumbered with casts, charts, records, x-rays, and other paraphernalia necessary to convey relevant information about a person's dental condition and the intended goals of treatment.

Accordingly, extremely positive and useful results in record-keeping, diagnosis, treatment, and counseling would be realized by consolidating the information about a person's dental condition and simplifying the presentation of such information in the tools used by orthodontists and maxillofacial surgeons. These results are realized by adaptation of an articulator apparatus to visibly denote the present positions of a person's teeth and jaws with respect to intended post-treatment goals. Stated another way, there is a need for an articulator-mounted dental model that visually integrates both the pretreatment condition of a person's teeth and jaws as well as the intended goals to be achieved by treatment of the condition.

SUMMARY

Visibly coding components of an articulator apparatus that mount maxillary and mandible casts enables visualization of the present positions of a person's teeth and jaws with respect to post-treatment goals. From another aspect, the visible coding indicates at least a direction, and preferably, a direction and a distance, which a person's teeth and/or jaws must be moved to achieve the goals.

DETAILED DESCRIPTION

U.S. Pat. No. 5,842,857, which describes and illustrates an articulator apparatus, is a useful reference with which to understand the principles and examples to be disclosed herein. Although the described articulator apparatus is called "an occlusofacial simulator", this is not intended to limit application of the visible coding that is to be described only to such a apparatus. In fact, the principles to be presented are broadly applicable to articulators that model the pre, intra, and post-treatment condition of the teeth and jaws of a person to aid orthodontists, maxillofacial surgeons, and other practitioners in being aware of a person's condition relative to a specified head plane, to each other, and to the jaw joints.

The principles of visual coding to be described rely on the Six Elements System of orthodontic analysis and diagnosis for examples and representative embodiments. However, this reliance is for purposes of illustration only and is not intended to limit the scope of the claims that follow.

Figure 1:
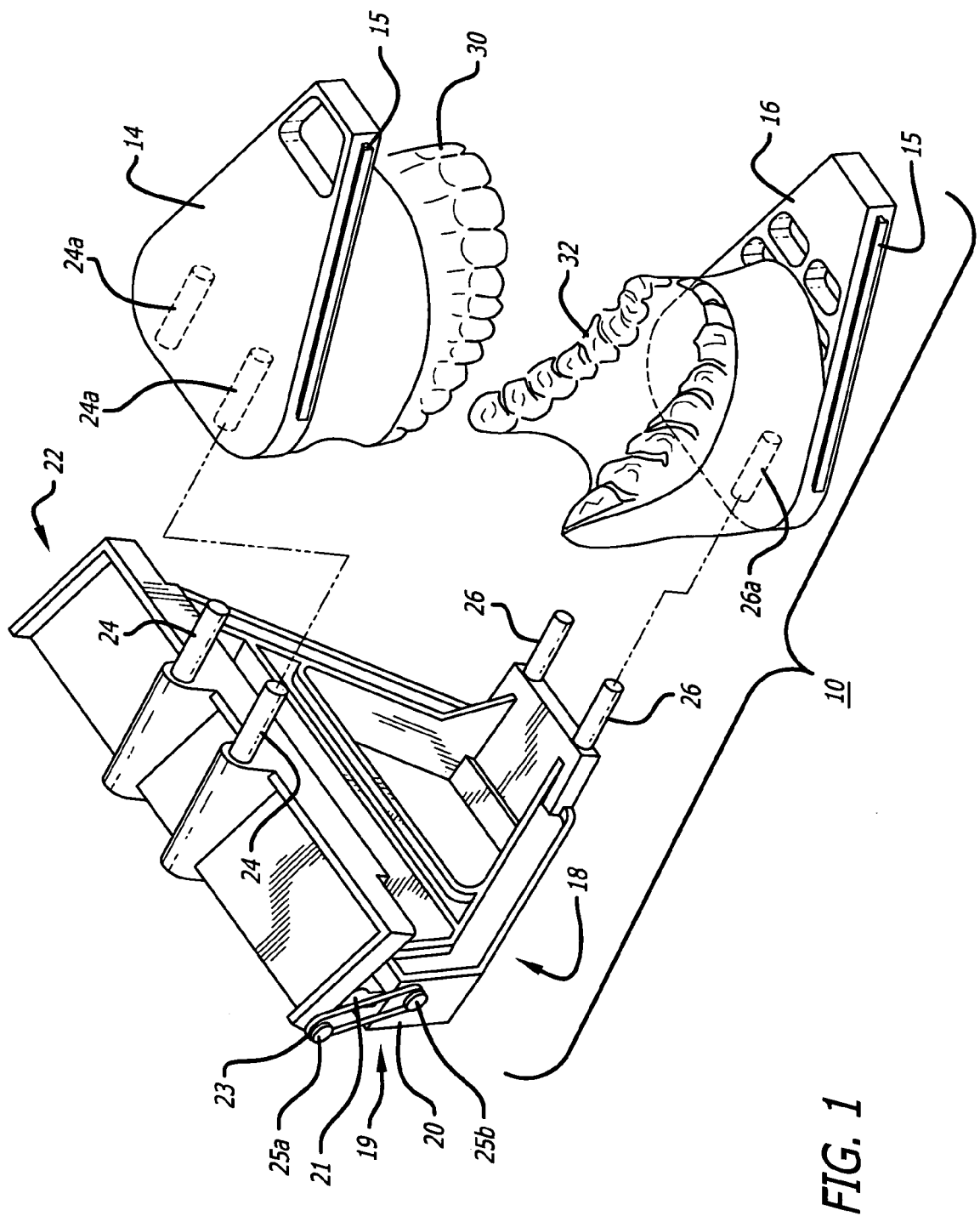
FIG. 1 is a partially exploded perspective view of an articulator apparatus showing components of the apparatus.
Figure 2:
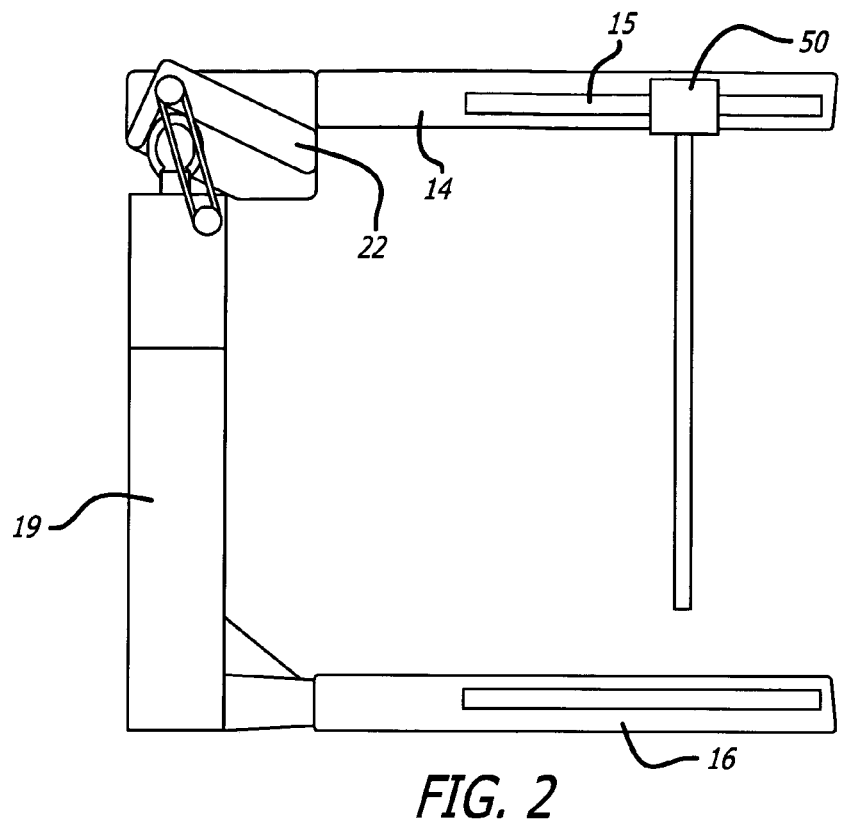
FIG. 2 is a partially schematic, side elevation view showing an articulator apparatus with a GALL rod mounted thereto.

With reference to FIGS. 1 and 2, an articulator apparatus 10 is illustrated. Components of the articulator apparatus 10 include a first cast support member 14, a second cast support member 16, and a frame 18 including a lower member 19 and an upper member 22. Each cast support member includes an elongate rail 15. Preferably, although without limiting the application of the principles of visible coding to be described, the components 14, 16, 19 and 22 may be formed by molding plastic with other materials. The lower member 19 has pedestals 20 on which transversely-disposed bulbs 21 are mounted. The upper member 22 is supported on the bulbs 21 and is hingedly connected at its lateral extremities to the lower member 19. The hinge connections are identical. The hinge connection visible in FIG. 1 includes a rubber band 23 stretched around a trunnion 25a on a respective lateral extremity of the upper member 22 and a trunnion 25b on the lateral extremity of the lower member 19. Each bulb 21 simulates a respective male portion of the TMJ. The bulbs 21 together permit pivotal movement between the lower member 19 and the upper member 22.

With further reference to FIGS. 1 and 2, the upper member 22 includes a pair of spaced apart, generally parallel posts 24 that are perpendicular to the frontal plane of the member. The lower member 19 includes a pair of spaced apart, generally parallel posts 26 that are perpendicular to the frontal plane of the lower member. For example, the posts 24 and 26 may be stainless steel rods that are incorporated into the molding process by which the upper member 22 and lower member 19 are formed. Each of the first and second cast support members 14 and 16 includes spaced apart, generally parallel tubular recesses 24a and 26a which enable the first and second cast support members to be received and slidably retained on the frame 18 by the posts 24 and 26.

Still considering FIGS. 1 and 2, when frame 18 and cast support members 14 and 16 are assembled as just described, the first cast support member 14 and the upper member 22 simulate a transverse section of the cranial base of a human skull on which a maxillary cast 30 taken from a person to be treated is supported. The second cast support member 16 simulates the person's mandible and, with the lower member 19, supports a mandibular cast 32 also taken from the person. With the support members 14 and 16 mounted to the frame 18, and the rubber bands 23 stretched over the trunnions 25a and 25b, the maxillary cast 30 is cemented to the support member 14. The articulator is inverted and the mandibular cast 32 is placed on the maxillary cast 30 and aligned therewith by means of a sheet of wax into which the person has bitten when the casts are made. The sheet of wax is sandwiched between the cusps of the casts 30 and 32. The mandibular cast 32 is then cemented to the mandibular support member.

Figure 3:
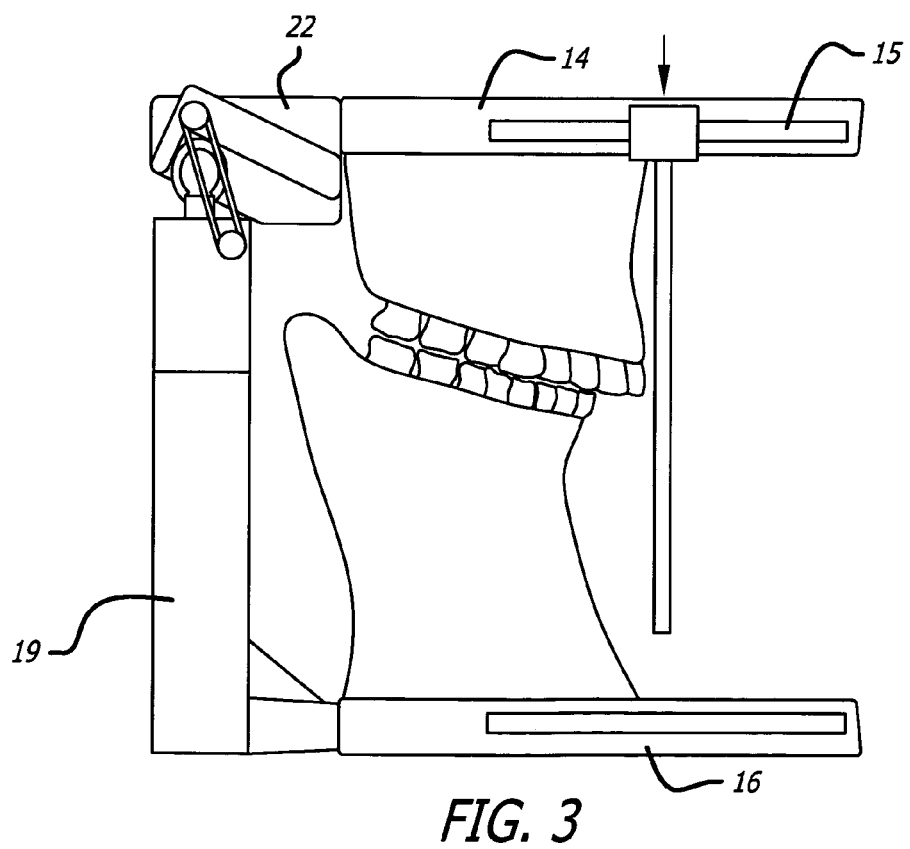
FIG. 3 is a side elevation view of an articulator apparatus with maxillary and mandibular casts mounted thereto showing an example of visibly coding apparatus components for post-treatment goals.

As shown in FIG. 3, with the casts 30 and 32 mounted to the articulator apparatus 10 as described, the casts, when brought together, are oriented to each other, to the simulated TMJs, and to the planes of the apparatus 10 just as the teeth of the person from whom the casts are obtained are oriented to each other, the person's TMJs, and the planes of the person's head. After alignment of the casts and diagnosis of the person's condition, limits for movement of teeth and/or jaws can be seen by viewing X-rays of the head and the mounted casts. Of course, the fossae of the simulated TMJs display the distal border of the oral complex for the male portions of the mandible. The anterior border of the oral complex can be displayed by a GALL rod 50 (seen in FIGS. 2 and 3) attached to the rail 15 of the maxillary cast support member 14 as taught in U.S. Pat. No. 5,176,515. The GALL rod 50 is used to indicate what the diagnosis proves to be the post-treatment or intended AP (border) goal for arch and jaw positions.

However, without the GALL rod there would be no way for the articulator to convey any information relevant to how much a person's teeth and jaws must be repositioned in order to approach or achieve post-treatment AP goals. The presence of such information on the articulator apparatus would be useful to either or both of an orthodontist and a maxillofacial surgeon in visualizing the status of a person's condition relative to specified goals. Such information would also be useful in counseling patients because of the instinctive understanding that the three-dimensional model imparts. The solution to this problem is to provide a visible code on articulator components to indicate the relative correspondence between the present positions of a person's teeth, arches and/or jaws as represented by casts mounted to the apparatus and the positions to which the teeth and jaws should be moved by treatment to achieve post-treatment goals. For example, the post-treatment goals may be one or more of the optimal goals for the person relative to the Six Elements of Orofacial Harmony, and/or compromise goals that are less than optimal. From another aspect, the visible code on articulator components is used to indicate the direction a person's teeth, arches and/or jaws should be moved by treatment to achieve post-treatment goals. The code system may include a color, a pattern of colors, a mark, a pattern of marks, a symbol, a pattern of symbols, or equivalent that is visible at, on, or in (denoted collectively as "on", for convenience) one or more surfaces of an articulator component.

EXAMPLE I

For example, a visible coding system using a color on articulator components may be provided to convey information about the relative correspondence between present positions of a person's teeth, arches, and/or jaws and treatment goals. Thus, a color may denote jaw position, or required direction of jaw movement during treatment, with respect to the optimal position for that person, or to a compromise position. As an illustration of such a coding system, an articulator component may have a color to indicate the relative position between the jaw modeled by a cast (hereinafter, "the jaw") mounted to or supported by it and an optimal AP position for that jaw. For this example, the colors green, red, and black may be used to code part or all of the lower member 19 and upper member 22. The lower member may be green, red, or black and the upper member 22 may be green, red, or black. In this code system, green indicates that the jaw is in an acceptable location with respect to the post-treatment position. Red signifies that the jaw is anterior to an optimal post-treatment AP position, which implies that the jaw must be moved posteriorly (back) to or toward the optimal AP position. And, black indicates that the jaw is posterior to the optimal post-treatment AP position for the jaw, which implies that the jaw is to be moved anteriorly (forward) to or toward the optimal AP position. This example is illustrated in FIG. 3 where the angled line hatching denoted by "G" signifies that at least a portion of the upper member 22 is colored green to show that the maxilla's AP position is correctly positioned and does not need to be moved, and the stippled shading denoted by "B" signifies that at least a portion of the lower member 19 is colored black to indicate that the mandible's AP position is posterior to its intended post-treatment position and is to be moved anteriorly. This example is not intended to be limiting as additional or other colors may be used, and additional or other articulator components (such as the cast support members) may be color coded. In the case of an articulator component fabricated by molding, a color reagent may be added to the material to be molded. Color can also be applied to one or more surfaces of an articulator component by painting, staining, or any equivalent process.

EXAMPLE II

For another example, a visible code system using a visible marking, such as a pattern of colors, figures, or symbols, on articulator components may be provided to convey information about the relative correspondence between the present positions of a person's jaws and a post-treatment position that may be the optimal position for that person, or a compromise position. In this regard, an articulator component may be marked on or in one or more surfaces with a pattern of elementary shapes to convey the information. For this example, patterns of arrows, dots, triangles, and stars written or formed on or in one or more surfaces may be used to visibly code the lower member 19 and upper member 22. In this scheme, and according to this example, a pattern of dots may indicate that the jaw is anterior to an optimal post-treatment position, which indicates that the jaw is to be moved posteriorly (back) to the intended post-treatment position. A pattern of triangles may indicate that the jaw is in an acceptable location with respect to the post-treatment position. And, a pattern of stars may signify that the jaw is posterior to its intended post-treatment position and is to be moved anteriorly (forward) to the intended AP position. This example is not intended to be limiting as additional or other patterns of colors (stripes, plaids, meshes) and/or figures (geometric shapes) and/or symbols (alphanumeric characters, words, numbers) may be used, and additional or other articulator components (such as cast support members) may be visibly coded. In the case of an articulator component fabricated by molding, a mold may be made that includes provision for forming figures or symbols on one or more surfaces of an articulator component, or the visible marking can be applied to the molded articulator component by painting, inscription, stamping, or equivalent.

Figure 4:
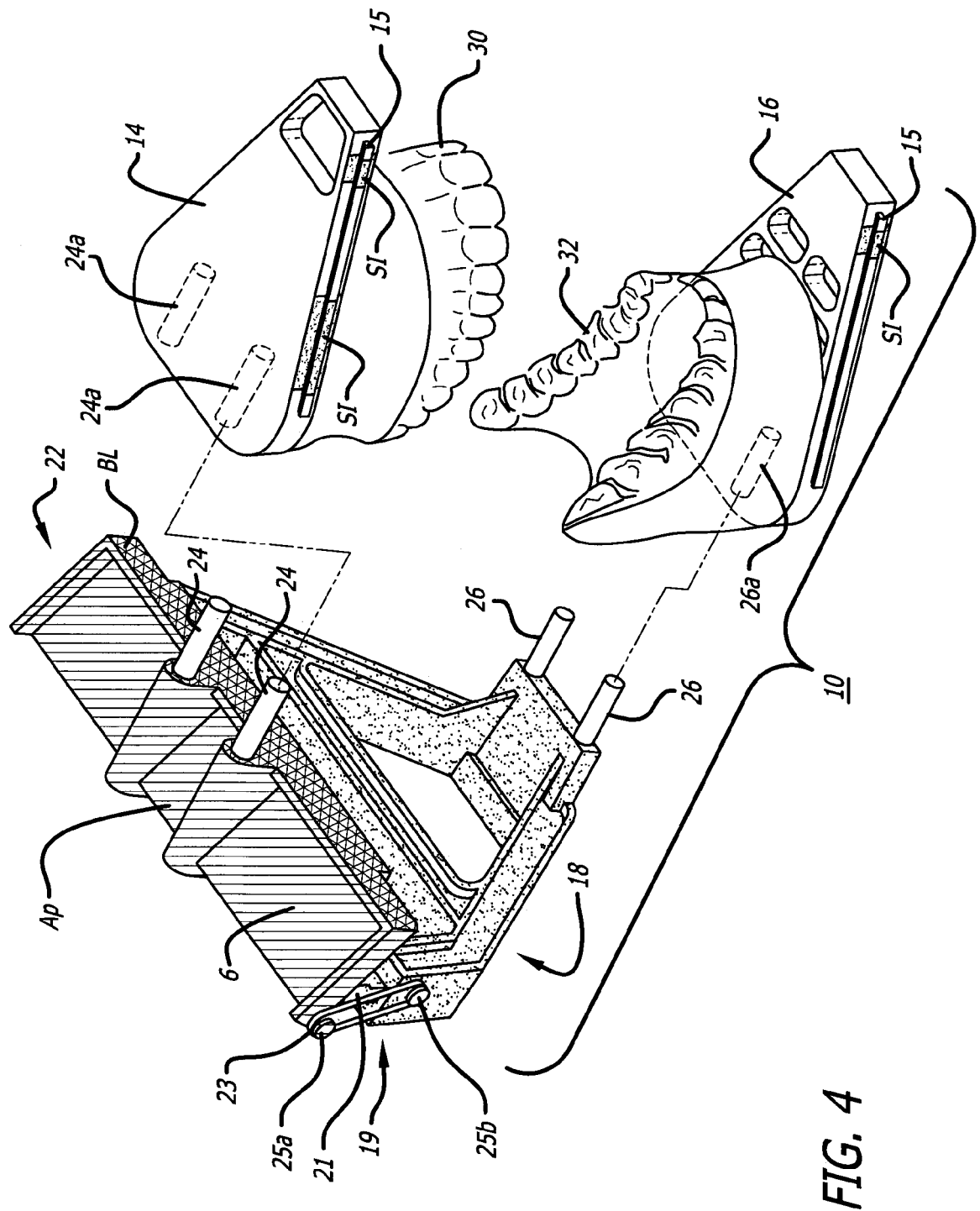
FIG. 4 is a partially exploded perspective view of an articulator apparatus showing an example of visibly coding articulator components.

Other examples and possibilities of the principles described herein will occur to the skilled practitioner. For example, using Six Element analysis, post-treatment goals may include, without limitation, optimal or compromise AP jaw position, optimal or compromise buccolingual (BL) jaw position, optimal or compromise superioinferior (SI) displacement of the maxilla, and others. Furthermore, a coding system that visibly marks articulator components may enable visualization of the positions of a person's jaws with respect to more than just one post-treatment goal. For example, with reference to FIG. 4, the lower member 19 may be coded as described above, while various surfaces of the upper member 22 may be coded for maxillary jaw movement to AP and BL post-treatment positions. Thus, the portion of the upper member 21 denoted by AP is colored green to indicate the maxilla is correctly positioned with respect to an optimal (or compromise) AP position. However, another portion of the upper member 21 may be visibly coded for another treatment goal. For example, the portion of the upper member denoted by BL may be colored (represented by the cross-hatching) to indicate whether movement of the maxilla is required in some direction in order to achieve an optimal or compromise buccolingual position. Further, as shown in FIG. 4, portions of the cast support members 14 and 16 may also be visibly coded for movement of the maxilla and mandibula to SI jaw positions.

An optional aspect may include providing a notation on a coded articulator component indicating a distance that teeth, an arch or a jaw must be moved in the direction indicated to reach the specific goal. Preferably, the notation is numerical, and the measurement is metric. For example, with reference to FIG. 4, the numeral "6" in the section or portion of the lower member 19 coded for the AP goal would indicate that the mandible is to be moved 6 mm anteriorly, according to the black coding of the section. That is to say that the distance from the present position of the mandible to the intended position is 6 mm.

As a practical matter, articulator components with visible coding may be mass produced by an appropriate manufacturing process in which identical components with identical coding would be fabricated in lots or runs. Alternatively, articulator components may be manufactured with codes for the more frequently-occurring conditions and separate coding components (colored adhesive strips, for example) for the less-frequently-occurring conditions could be provided. Respective sets of identical components with identical markings would be assembled and packaged. Kits may be prepared that include all of the components necessary to assemble one or more articulators, in which sets of coded articulator components and separate sets of coding components are provided. Thus, for example, the articulator apparatus 10 of FIG. 1 may be provided as a kit including black, green, and red lower members, black, green, and red upper members, non-coded (white, for example) cast support members, and colored adhesive strips. Instead of, or in addition to kits, individual lots of identical, identically coded components could be sold, purchased, or inventoried. For example, an orthodontic clinic may order and stock separate lots of black, green, and red lower members, black, green, and red upper members, and non-coded (white, for example) cast support members. The treatment plan would indicate which components would be selected from stock.

Although visible coding of articulator components has been described with reference to preferred embodiments and specific examples, it should be understood that various modifications can be made without departing from the principles disclosed herein, which are limited only by the following claims.

I claim:

1. A method for assembling an articulator apparatus using jaw cast support components colored to indicate correspondence between a current position of a jaw and a post-treatment position for the jaw, comprising:
    determining a current position of the jaw with respect to a post-treatment position for the jaw;
    selecting a first jaw cast support component having a color selected from the group including a first color indicating that the jaw is in an acceptable location with respect to the post-treatment position, a second color indicating that the jaw is anterior to a post-treatment AP (anteroposterior) position, and a third color indicating that the jaw is posterior to the post-treatment AP position; and
    connecting the selected first jaw cast support component to a second jaw cast support component.

2. The method of claim 1, further including making a cast of the jaw, and supporting the cast in the articulator apparatus with the first jaw cast support component.

* * * * *